United States Patent [19]

Couture et al.

[11] 4,365,102

[45] Dec. 21, 1982

[54] METHOD OF MANUFACTURING PERFLUOROMETHANE AND PERFLUOROETHANE

[75] Inventors: Maurice J. Couture, Parkersburg, W. Va.; Dan Hayashi, Shimizu, Japan

[73] Assignee: E. I. du Pont de Nemours and Company, Wilmington, Del.

[21] Appl. No.: 191,921

[22] Filed: Sep. 29, 1980

[51] Int. Cl.$^3$ ............................................. C07C 17/24
[52] U.S. Cl. .................................... 570/163; 570/173; 570/153
[58] Field of Search .......................... 570/163, 153, 173

[56] References Cited

U.S. PATENT DOCUMENTS

| | | | |
|---|---|---|---|
| 2,758,138 | 8/1956 | Nelson | 570/153 |
| 2,970,176 | 1/1961 | Ten Eyck et al. | 570/163 |
| 3,446,858 | 5/1969 | Shingu et al. | 570/153 |
| 3,873,630 | 3/1975 | West | 260/653.3 |
| 4,128,589 | 12/1978 | Pastor et al. | 260/653 |
| 4,137,055 | 1/1979 | Sulzbach et al. | 55/71 |

*Primary Examiner*—Charles F. Warren
*Assistant Examiner*—Joseph A. Boska

[57] ABSTRACT

A method of manufacturing $CF_4$ and/or $C_2F_6$ characterized by employing a mixed gas of tetrafluoroethylene and carbon dioxide at a mol ratio of less than 4:1 and heating it to a temperature exceeding 900° C.

2 Claims, No Drawings

METHOD OF MANUFACTURING PERFLUOROMETHANE AND PERFLUOROETHANE

FIELD OF THE INVENTION

This invention is directed to a method of manufacturing lower perfluoroalkanes and more specifically to a method of manufacturing perfluoromethane ($CF_4$) and perfluoroethane ($C_2F_6$) of high purity at a high yield by a safe and simple process either separately or in a mixed state of $CF_4$ and $C_2F_6$.

BACKGROUND

Lower perfluoroalkanes are useful as low temperature refrigerants or electrical insulating gases, and as etching agents for semi-conductors.

Methods of manufacturing lower perfluoroalkanes are known, such as:

(A) direct fluorination of carbon;

(B) fluorination or disproportionation of chlorofluoroalkane; and (C) fluorination or decarbonization of perfluoroalkene.

As an example of the method stated in (A) above, granulated carbon is fluorinated in the presence of fused metal fluoride (in this case, potassium fluoride) in the presence of chlorine (Japanese Toku Ko No. Sho 43-28089) as shown below:

$$C + 2CaF_2 + 2Cl_2 \rightarrow CF_4 + 2CaCl_2 \quad \ldots \quad (1)$$

However, this method is a reaction in a three phase state of solid, liquid and vapor, and as such, it is a complicated process. Also, it is difficult to control the reaction. Furthermore low conversion rates of raw materials to product are common, and, though not shown in formula (1), chlorofluoromethanes such as chlorotrifluoromethane ($CClF_3$), are produced as by-products, thus lowering the purity of the final product.

As an example of the method staged in (B) above, chlorofluoromethane is fluorinated in the vapor phase by using chromium fluoride as catalyst and hydrogen fluoride as fluorinating agent (U.S. Pat. No. 2,745,886), as shown below in equation 2, or chlorofluoromethane is disproportionated by using aluminum fluoride as catalyst (U.S. Pat. No. 2,478,201), as shown below in formula 3:

$$CCl_2F_2 + HF \rightarrow CClF_3 + CF_4 + HCl \quad \ldots \quad (2)$$

$$CCl_2F_2 \rightarrow CF_3Cl + CF_4 + CFCl_3 + CCl_4 \quad \ldots \quad (3)$$

$CF_4$ to be obtained by these methods is, as shown in formulae (2) and (3) above, in the form of a mixture with other chlorofluoromethane and therefore it is necessary to separate the chlorofluoromethanes. It is difficult to separate $CF_4$ from $CClF_3$ and the yield rate of $CF_4$ is as low as 10-20%.

On the other hand, the method stated in (C) above has an advantage that $CF_4$ of high purity can be obtained, but it is not satisfactory because of safety problems. The most typical reaction to obtain $CF_4$ from TFE is the decomposition reaction of TFE through disproportionation as shown below:

$$C_2F_4 \rightarrow CF_4 + C \quad \ldots \quad (4)$$

This reaction is of an explosive nature and is accompanied by the release of very large amounts of heat. It produces as a by-product a great deal of carbon, which sticks to the walls of reactor, thus making its industrial application difficult from the viewpoints of both safety and process.

Other reactions are known such as (U.S. Pat. No. 2,351,390);

$$C_2F_4 + O_2 \rightarrow CF_4 + CO_2 \quad \ldots \quad (5)$$

$$C_2F_4 + 2F_2 \rightarrow 2CF_4 \quad \ldots \quad (6)$$

Though these reactions have an advantage of producing no carbon, they have other defects such as production of heat 2.5-3.5 times greater than in equation (4), thus creating the possibility of explosion. Moreover, in formula (6) the elemental state of fluorine which is expensive and very high in reactivity is used. For these reasons, they have not been industrially adopted from safety and economic viewpoints.

SUMMARY OF THE INVENTION

The defects of the above-stated conventional methods have been overcome by a method for manufacturing $CF_4$ and/or $C_2F_6$ free from these defects by reacting a mixture of gaseous tetrafluoroethylene (TFE) and carbon dioxide ($CO_2$) at a mol ratio of TFE to $CO_2$ of less than 4:1 at a temperature higher than 950° C.

DESCRIPTION OF THE INVENTION

An advantage of the process of this invention is that lower perfluoroalkanes of high purity can be obtained at high yield and high conversion rates. The process of this invention is economical and advantageous in that operations for the recovery of raw materials from product and the separation of by-products from the products, are either not necessary or made to be simpler and easier.

Another advantage is that since the raw materials and products are all gases, control of the reaction is easy and the equipment used in the manufacture can be made simply.

Still another advantage of this invention lies in the safety of the process, since $CO_2$ acts as a diluent for TFE, thus reducing the chance of explosion due to the decomposition of TFE. The $CO_2$ also acts endothermically, thus greatly lowering the reaction heat.

One more advantage of this invention is that carbon is not produced, or is produced in very small amounts, thus the clogging of the reaction tube due to the adherence of carbon is prevented or retarded and troublesome cleaning operations are avoided.

The first two advantages mentioned above are mainly advantages over the direct fluorination of carbon and the fluorination or disproportionation of chlorofluoroalkane, while the last two advantages are advantages over the fluorination or decarbonization of perfluoroalkane. The fact that $CF_4$ and $C_2F_6$ can be manufactured either separately or in a mixed state is worthy of special mention as an advantage of this invention. In this invention, the product obtained is easily determined by simply changing reaction conditions as described in more detail later.

Conditions of Reaction

The reaction of this invention can be expressed by the following equations:

$$C_2F_4 + CO_2 \rightarrow CF_4 + 2CO \quad \ldots (7),$$

and $$3C_2F_4 + 2CO_2 \rightarrow 2C_2F_6 + 4CO \quad \ldots (8)$$

These reactions are affected by temperature, and mixture ratio of TFE and $CO_2$ used as raw materials.

(i) Reaction Temperature

The reaction temperature to be used in this invention is a temperature exceeding 900° C., preferably the range of 950°–1500° C. Within this range, if the mol ratio of TFE and $CO_2$ is 1:1, for instance, the reaction of equation (8), that is, $C_2F_6$ formation reaction, mainly takes place in the range of 950°–1050° C.; the reactions of formulae (7) and (8), that is, both $CF_4$ and $C_2F_6$ formation reactions proceed in the range of 1050°–1100° C.; and the reaction of formula (7) selectively takes place at the temperature higher than 1100° C., producing a high purity of $CF_4$. If the mixture ratio of TFE and $CO_2$ is 3:2, there is a tendency that the range of $C_2F_6$ formation temperatures expands to the side of higher temperatures. However, at temperatures lower than 900° C., the $CF_4$ formation reaction of equation (7), and the $C_2F_6$ formation reaction of equation (8) hardly proceed. In the range of 800°–850° C. the conversion reaction from TFE to hexafluoropropene (HFP) predominantly takes place as shown below:

$$3C_2F_4 \rightarrow 2C_3F_6 \quad \ldots (9)$$

This reaction is useful for the manufacturing method of HFP and is described in Tokukai No. Sho 49-48608.

The upper limit of temperature is not limitative and any temperature lower than the decomposition temperature of $CF_4$ can be used. However, since the use of too high a temperature would narrow the range of selecting the materials for the reaction tube and is not desirable from heat economics viewpoint, use of temperatures lower than 1500° C., preferably lower than 1300° C., are desirable.

(ii) Ratio of Reactant Gas (Mixed Gas of TFE and $CO_2$)

The process of this invention proceeds in the form of the equations shown in formulae (7) and (8) above and therefore, it is most desirable to use, in conformity with theoretical amount, mixed gas of TFE and $CO_2$ in the range of mol ratio 3:2–1:2, especially at 1:1, for the manufacture of $CF_4$; and in the range of 2:1–1:1 especially at 3:2, for the manufacture of $C_2F_6$ as reactant gases. However, the mixture ratio of TFE to $CO_2$ reactant gas to be actually used should be less than 4:1, preferably in the range of from 3:1 to 1:10.

There is a tendency that the use of gases whose mixture ratio exceeds 4:1 increases formation of carbon and increases the danger of explosion due to disproportionation of TFE.

Though the lower limit of the mixture ratio is not necessarily restrictive, the excess of $CO_2$ which is not involved in the formation reaction of $CF_4$ and $C_2F_6$ would merely be increased, thus being heat-economically disadvantageous. It is preferable, therefore, to set the mixture at least at more than 1:10.

(iii) Other Reaction Conditions and Equipment

The process of this invention can take place under pressure or reduced pressure. Since the reaction speed is comparatively fast, it is enough to increase the temperature of the gaseous mixture to a desired temperature and maintain it for from several seconds to several minutes.

As to reaction equipment, no special equipment is necessary, but such gas reaction equipment as is generally used for high temperature operation, for instance, a tube type of reactor, can advantageously be used.

Gaseous Products

The gaseous products to be obtained by the above-stated reactions consist of such main products as $CF_4$, $C_2F_6$ and CO as shown in formulae (7) and (8), by-products of $COF_2$, hexafluoropropene and other unknown fluorides and unreacted substance of $CO_2$.

Of these gaseous products, the formation of the by-products such as $COF_2$, hexafluoropropene (HFP) and other unknown fluorides which would cause the yield loss will tend to sharply decrease as reaction temperature goes up. For example, HFP and other unknown fluorides comprise about 5–8% by weight in case of reaction at 950° C., but are hardly detectable at 1000° C.; while $COF_2$ is present at about 45% by weight at 1000° C., but decreases to less than 10% by weight at 1150° C. and to about 2% by weight at 1300° C.

Purification

It is necessary to separate the by-products in the case of the reaction being carried out at lower temperatures, but such separation of by-products can be omitted in case of the manufacture of $CF_4$ to be conducted at higher temperatures.

Separation of the main products from $COF_2$ by-product can be done by contact with water to decompose the $COF_2$ into HF and $CO_2$. Separation of organic fluorides such as hexafluoropropene can be achieved by distillation.

CO can be separated by oxidation to $CO_2$, and absorption together with unreacted $CO_2$ into alkali solution, or by absorption of CO itself into copper-ammonia complex salt.

EXAMPLES

Into a 300 mm long, 10 mm OD and 9.4 mm ID platinum reaction tube fitted into an electric tube type furnace (high temperature type) IRH made by Ishizuka Electric Works, Ltd., was placed the mixed gas of TFE and $CO_2$.

The equipment was operated so that the mixed gas would stay in the reactor for about a minute at 23° C. under one atmospheric pressure. The reaction temperature was measured with a platinum/platinum-rhodium thermocouple fitted to the outer surface of the reactor.

The gaseous products obtained were collected and their compositions were analyzed by gas chromatography. The compositions of reactant gases and product gases and reaction conditions are shown in the following table.

TABLE

| Experiment Number | 1 | 2 | 3 | 4 | 5 |
|---|---|---|---|---|---|
| Reactant gas | | | | | |
| TFE/$CO_2$ (mol ratio) | 1/1 | 1/1 | 1/1 | 1/1 | 3/2 |
| Reaction Conditions | | | | | |
| Flow of Reactant Gas (ml/min) | 23 | 23 | 23 | 23 | 23 |
| Reaction Temp. (°C.) | 1000 | 1075 | 1150 | 1300 | 1100 |
| Composition of Gaseous Products | | | | | |
| $CO_2$ (mol %) | 13.5 | 7.7 | 4.1 | 3.2 | 4.4 |
| CO (mol %) | 39.6 | 52.5 | 60.2 | 62.6 | 48.4 |

TABLE-continued

| Experiment Number | 1 | 2 | 3 | 4 | 5 |
|---|---|---|---|---|---|
| Fluorides (mol %) | 46.9 | 39.8 | 35.7 | 34.2 | 47.2 |
| Composition of Fluorides in Gas Products | | | | | |
| $CF_4$ (% by wt.) | 1.6 | 38.8 | 91.5 | 97.9 | 19.9 |
| $C_2F_6$ (% by wt.) | 53.9 | 27.5 | 0.8 | 0.1 | 61.3 |
| $COF_2$ (% by wt.) | 44.3 | 33.5 | 7.5 | 2.0 | 18.6 |
| Other Fluorides (% by wt.) | 0.2 | 0.2 | 0.2 | trace | 0.2 |

We claim:

1. A method of manufacturing $CF_4$ and $C_2F_6$ which comprises heating tetrafluoroethylene and carbon dioxide at a mol ratio of TFE to $CO_2$ in the range of 3:1 to 1:10 at a temperature in the range of 1100° C. to 1300° C. and separating the resulting products.

2. The method of claim 1 in which the mol ratio of TFE to $CO_2$ is in the range of 3:2 to 1:2.

* * * * *